US008961561B2

(12) United States Patent
Schulman (10) Patent No.: US 8,961,561 B2
(45) Date of Patent: Feb. 24, 2015

(54) SURGICAL SYSTEM INCLUDING SUTURE ANCHOR AND INSERTION DEVICE AND METHOD FOR USING (76) Inventor: Daniel S. Schulman, Phoenix, AZ (US)

( * ) Notice: Subject to any disclaimer, the term of this patent is extended or adjusted under 35 U.S.C. 154(b) by 668 days.

(21) Appl. No.: 12/868,625

(22) Filed: Aug. 25, 2010

(65) Prior Publication Data
US 2012/0053622 A1 Mar. 1, 2012

(51) Int. Cl.
A61B 17/04 (2006.01)
A61B 17/88 (2006.01)

(52) U.S. Cl.
CPC .......... *A61B 17/0401* (2013.01); *A61B 17/0483* (2013.01); *A61B 17/8805* (2013.01); *A61B 2017/0403* (2013.01); *A61B 2017/0409* (2013.01); *A61B 2017/0414* (2013.01); *A61B 2017/0496* (2013.01)
USPC .......................................................... 606/232

(58) Field of Classification Search
USPC .......................................................... 606/232
See application file for complete search history.

(56) References Cited

U.S. PATENT DOCUMENTS

| | | | | |
|---|---|---|---|---|
| 5,176,682 | A * | 1/1993 | Chow | 606/232 |
| 5,733,307 | A | 3/1998 | Dinsdale | |
| 6,508,830 | B2 * | 1/2003 | Steiner | 606/232 |
| 6,610,079 | B1 * | 8/2003 | Li et al. | 606/232 |
| 6,641,597 | B2 | 11/2003 | Burkhart et al. | |
| D605,763 | S | 12/2009 | Griffis, III et al. | |
| 7,776,041 | B1 * | 8/2010 | Walters | 606/86 R |
| 8,075,588 | B2 * | 12/2011 | Berberich et al. | 606/232 |
| 2003/0204193 | A1 * | 10/2003 | Gabriel et al. | 606/139 |
| 2005/0075636 | A1 | 4/2005 | Gotzen | |
| 2007/0021751 | A1 | 1/2007 | Reay-Young et al. | |
| 2008/0109037 | A1 | 5/2008 | Steiner et al. | |
| 2010/0082072 | A1 | 4/2010 | Sybert et al. | |
| 2010/0326452 | A1 | 12/2010 | Gall | |

OTHER PUBLICATIONS

Munting, Everard et al., "Effect of sterilization on osteoinduction," Acta. Orthop. Scand. vol. 59(1), pp. 34-38 (1988).
Eichhorn, Philip J., "Suture/Eyelet Orientation Effects on Bone Anchor Failure Strengths: Improving Surgical Repair of Tendons Torn Off Bone," Journ. of the Mississippi Acad. of Sci. vol. 45(3), pp. 196-203 (Jul. 2000).

(Continued)

*Primary Examiner* — Gregory Anderson
*Assistant Examiner* — Christina Lauer
(74) *Attorney, Agent, or Firm* — Etherton Law Group, LLC (57) ABSTRACT An improved suture anchor has one or more channels formed into the exterior surface of the anchor body. The channels may be used to inject a compound, such as filler material or an adhesive, into the implant site. Preferably, the channels connect to a retainer in the anchor body for a suture to pass through, preventing the suture from being compressed and allowing removal and adjustment of a suture retained by the anchor after the anchor is installed in a bone. The retainer is preferably a slot formed into the distal end of the anchor body. In a method of securing tissue to bone, an insertion tool is used to insert the suture into the anchor and install the anchor into an implant site in the bone. If the suture later fails, the channels may be used to fill the implant site with bone cement for redrilling. Preferably, the suture anchor is made of human cortical bone or a similarly bioabsorbable and osteoconductive material.

3 Claims, 9 Drawing Sheets (56) References Cited

OTHER PUBLICATIONS

Barber, F. Alan, "Sutures and Suture Anchors—Update 2006," Arthroscopy vol. 22, Issue 10, pp. 1063-1069.e2 (Oct. 2006) (Abstract only).
"ALLOFIX Biologic Suture Anchor," last retrieved from http://mtfsports.org/allofix.html on Aug. 16, 2010.
Parisien, J. Serge, Current Techniques in Arthroscopy, Third Edition, Chapter 8, pp. 71-78 (1998).
Albrektsson, T. et al., "Osteoinduction, osteoconduction and osseointegration," Eur Spine J 10:S96-S101 (2001).
Murphy, Lara J. et al., "Essential Insights on First MPJ Implant Revision," Podiatry Today vol. 21 Issue 5 (May 1, 2008), last retrieved from http://www.podiatrytoday.com on May 12, 2011.
Mauntler, Nathan A., "Dimensional Study of an Interference Fit Allograft," graduate thesis, University of Florida 2006.
Oshtory, Rayshad et al., "Bioabsorbable Tricalcium Phosphate Bone Cement Strengthens Fixation of Suture Anchors," article, Clin. Orthop. Relat. Res. 468:3406-3412 (Jun. 3, 2010).
"Bioknotless RC Anchor," Instruction Booklet, DePuy Mitek, Inc., Feb. 2008, pp. 1-7.

* cited by examiner

SURGICAL SYSTEM INCLUDING SUTURE ANCHOR AND INSERTION DEVICE AND METHOD FOR USING

FIELD OF INVENTION

This invention relates to methods and devices for attaching tissue to bone. This invention relates particularly to a suture anchor that is installed in bone.

BACKGROUND

The field of orthopedic surgery addresses the need to reattach tissue, particularly connective tissue such as tendons and ligaments, to bone following detachment due to injury or surgery. One approach that is commonly used is to install an implant in the bone at the reattachment site. The tissue is then tied to the implant with one or more lengths of suture. Eventually, the tissue heals by reconnecting to the bone. The implant, known as an anchor, and the sutures may be left in the body or removed.

There are several drawbacks to this procedure. Commonly-used materials for an anchor include metals, plastics, and other nonorganics that may cause adverse biochemical reactions in the body, such as bone and tissue necrosis and other damage, rejection of the implant by the body, and release of toxins into healthy tissue, bone marrow, or the blood stream through degradation of the implant. Additionally, these materials are not bioabsorbable or osteoconductive, so their permanent implantation may prevent the bone from fully healing. It would be advantageous to develop a suture anchor that has more favorable biochemical properties.

Another drawback with most existing anchors relates to securely fastening the anchor, and thereby the suture, to the bone. Some anchors are threaded like a screw and therefore are screwed into the bone, with the threads essentially cutting into the bone to secure the anchor. This can traumatize or otherwise damage the living bone when inserted and removed. Additionally, most anchors are loaded with suture before insertion. If the anchor must be twisted to seat it in the bone, pre-loaded suture will also be twisted, potentially damaging the suture. Other anchors are ribbed and are forced into a hole in the bone that is slightly smaller in diameter than the ribs. While this design may not twist the suture, it may still traumatize or otherwise damage the surrounding bone, and may also damage the anchor due to the force required to fully insert the anchor.

Push-in anchors are known to be substantially the same size as the hole into which they are inserted. Most such anchors are then secured by an adhesive. Using an adhesive, however, is potentially messy and expensive, requires an additional step, and may not be an option at all if the anchor is a temporary implant. An anchor that can be secured in place without these problems is needed.

These problems have been recently addressed using suture anchors made of bioabsorbable, osteoconductive material, including human cortical bone. These materials are absorbed by the living bone as new bone tissue develops around the implant and into its porous body. Additionally, these materials do not damage the living bone or tissue, do not release toxins, are far less likely than nonorganic materials to be rejected by the body, and allow the bone to fully heal. Typically, cortical bone material is pulverized and used as an additive in molding the anchor, but certain anchor designs made from whole cortical bone are known. For example, the Musculoskeletal Transplant Foundation produces the ALLO-FIX® line of biologic suture anchors, which are machined from cortical bone of the tibia or femur of a human cadaver. It has been shown that the ALLOFIX® suture anchors are fully incorporated into the surrounding live bone and are no longer visible on x-ray films within four months of implantation. Further, it has been shown that allogenic cortical bone will naturally expand by about 3% of its size when it is inserted and contacts living bone. The mechanism of this expansion is not fully understood, but is believed to be caused largely by hydrolysis, due to the porosity of the cortical bone. The expansion of the anchor is sufficient to secure it in place, so that a push-in anchor may be used without adhesive. The expansion also encourages osteoconduction from the living bone to the anchor.

While these relatively new implants exhibit improved biochemical properties over nonorganic designs, they continue to suffer from other design drawbacks. One problem involves the use of an eyelet attached to or passing through the anchor for securing the suture to the anchor. Some anchors have eyelets attached at the top of the anchor, much like the head of a needle. These eyelets are prone to breaking off, and otherwise prevent insertion of the anchor so it is flush with the bone, because the eyelet protrudes. In other anchors, such as the ALLOFIX® anchors, the eyelet is a tunnel through the anchor body. These anchors secure the suture in place by wedging it between the anchor and the bone during insertion, a process known as interference fit. Interference overcomes the problems with protruding eyelets, but unfortunately creates a potentially more hazardous problem in "pinching" the suture. Specifically, the tensile strength of the suture may be dramatically reduced where it is pinched, and some sutures may be observably damaged when pinched due to their thickness or composition. Another drawback is the difficulty, and often impossibility, of repositioning a suture or removing a broken suture without removing the anchor. An anchor that securely retains the suture and accommodates all types of sutures without reducing the tensile strength of the suture is needed.

Through all approaches to suture anchors, a key design element is the anchor's resistance to the high tensile forces often imparted by connective tissue. The most problematic anchor susceptibilities are referred to as bending, which is the anchor's resistance to becoming concave or convex; shear, which is the anchor's resistance to lateral breakage; and pull-out, which is the anchor's resistance to being withdrawn from the insertion hole. A suture anchor that addresses the drawbacks of existing anchors while maintaining acceptable resistances is desired.

Therefore, it is an object of this invention to provide an apparatus to reattach tissue that has become detached from bone. It is a further object that the device be composed of a material that is not harmful to the body. Another object of this invention is to provide an attachment device that does not damage the bone as it is inserted. A further object is to provide a suture anchor that may be used with any suture. A further object is that the suture anchor allows easy repositioning and removal of an attached suture. Another object is that the suture anchor does not reduce the tensile strength of the suture when inserted. Another object is to provide a method of attaching tissue to bone using a bioabsorbable suture anchor without reducing the tensile strength of the suture.

SUMMARY OF THE INVENTION

A suture anchor is installed in bone and receives a suture which is in turn attached to tissue, such as a tendon, capsule, or ligament, creating a temporary or permanent attachment of the tissue to the bone. The anchor is preferably cylindrical, most preferably having planar ends. The anchor is preferably made out of a bioabsorbable material, most preferably human cortical bone, or another osteoconductive material capable of incorporation with the living bone to which it is anchored. Chemical reactions from direct contact with the living bone cause the anchor to expand, securing the anchor in place until the anchor is incorporated into the living bone.

The anchor has a retainer formed into the anchor body. The retainer receives a suture and holds the suture in place. In the preferred embodiment, the retainer is a slot formed into the end of the anchor body that goes into the bone, so that the suture is retained behind the anchor when the anchor is installed. One or more channels are formed into the anchor body, running substantially parallel to the axis of the anchor body and connecting to the retainer. The suture may pass through these channels and out of the bone, so that the tensile strength of the suture is not affected by compression forces, such as in interference fit. The channels may be used to adjust the placement of a loaded suture by pulling one of the loose ends. Additionally, the channels may be used to deliver filling material into the hole behind the anchor as needed. In an alternative embodiment, the retainer may be an eyelet through the anchor body, and the channels connect to the eyelet.

To attach the tissue to the bone, a hole may be drilled in the bone to receive the anchor. An insertion tool may be used to load the suture into the anchor and then insert the anchor into the hole. The sutures may be repositioned through the channels in the anchor, and are then attached to the tissue by conventional means. A broken suture may be removed by pulling it through the channels, and the channels and retainer may be filled with bone cement or another compound so that the insertion site may be reused for anchoring if needed.

DETAILED DESCRIPTION OF THE INVENTION

Referring to FIGS. 1-6, there is illustrated the preferred embodiment of the present invention, designated generally as 10, which is a suture anchor that is implanted in a living bone so that one or more retained sutures 40 may be used to attach tissue to the bone. The anchor 10 comprises an anchor body 11 having a proximal end 12 and a distal end 13. The anchor 10 is inserted into the bone distal end 13 first. The anchor 10 may be any size and shape that is capable of anchoring the target tissue to the target bone, including cylindrical, prism-shaped with any two-dimensional shaped base, pyramidal, conal, or a combination of such shapes. For example, in a first embodiment illustrated in FIGS. 1-3, the anchor body 11 is substantially bullet-shaped, having a cylindrical portion starting at the proximal end 12 and tapering from a first diameter D to a second diameter D' at the distal end 13. Preferably, the anchor body is cylindrical with planar ends 12, 13 that are orthogonal to the axis A-A of the cylinder. See FIGS. 4-6. The exterior surface of the anchor body 11, being the surface that contacts the living bone on insertion, is preferably substantially smooth, but may comprise projections designed to secure the anchor 10 to the living bone, such as ribs or threads. In other embodiments, one or both of the proximal end 12 and distal end 13 may be non-planar, such as concave, convex, or tapered. Further, if one or both of the proximal end 12 and distal end 13 are planar, the plane of each planar end may be non-orthogonal to the axis A-A of the anchor body 11, to a degree that is beneficial for the implementation.

The proximal end 12 may have an insertion guide 17 formed into its surface. The insertion guide 17 helps a physician position an insertion tool properly on the proximal end 12 to insert the anchor 10 into the bone. In the embodiment shown, the insertion guide 17 is a set of orthogonal grooves formed into the proximal end 12. The insertion tool for this embodiment has corresponding projections formed into the surface that contacts the anchor 10 for insertion. The insertion guide 17 may have any desirable configuration, including a configuration that is specific to a certain model of insertion tool, or a configuration that is usable by several different insertion tools. The preferred insertion guide 17 corresponds to the insertion tool 50 described below.

Figure 1:
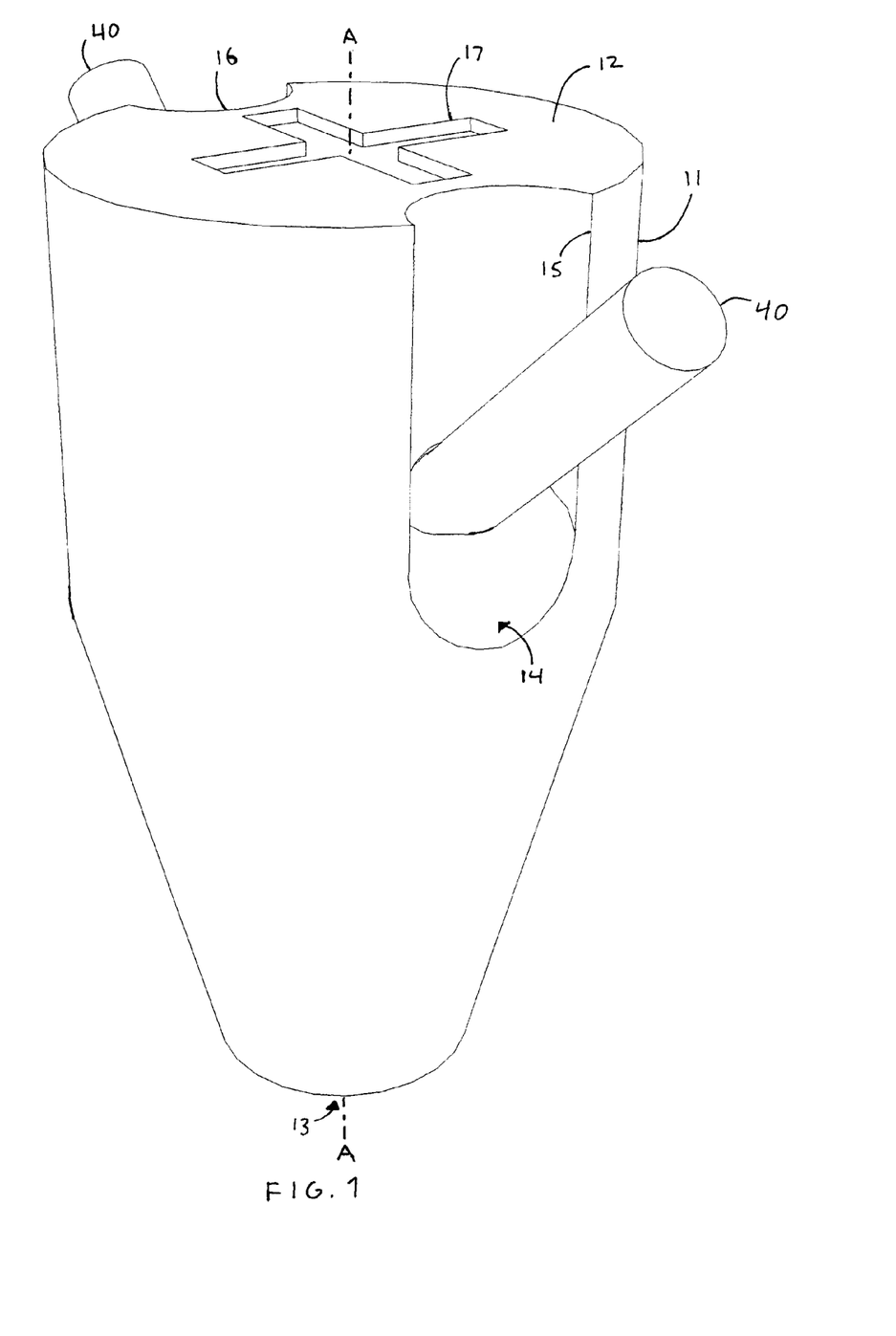
FIG. 1 is a side perspective view of a first embodiment of a suture anchor with a length of suture loaded in the anchor.
Figure 2:
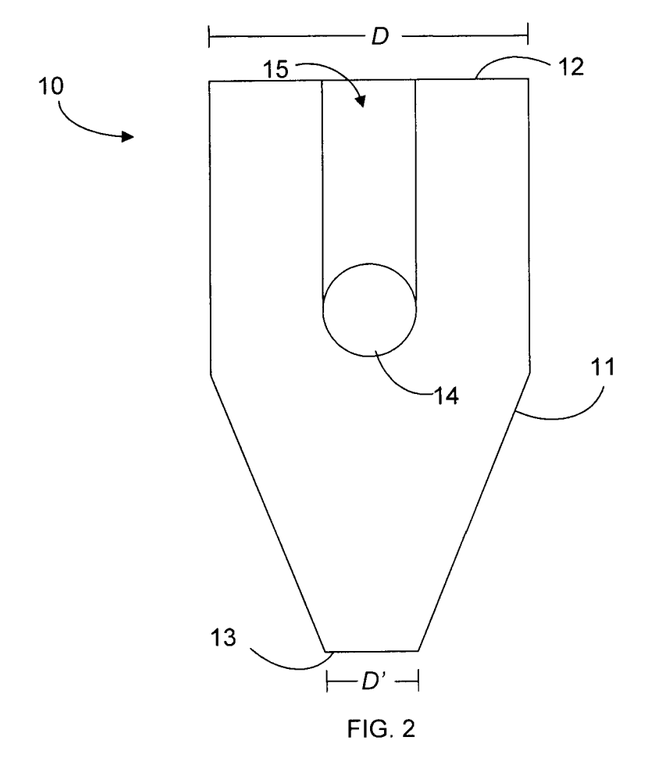
FIG. 2 is a right side view of the suture anchor of FIG. 1.
Figure 3:
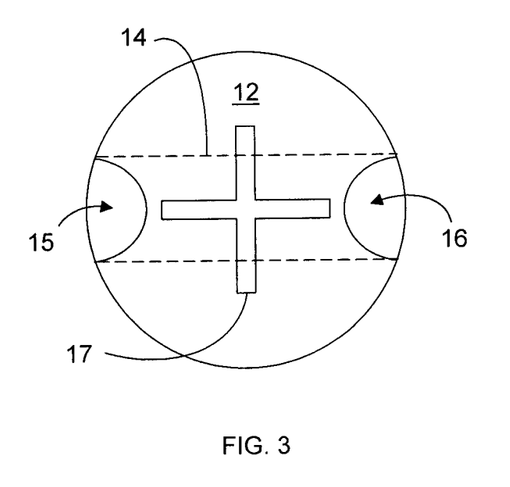
FIG. 3 is a top view of the suture anchor of FIG. 1.
Figure 4:
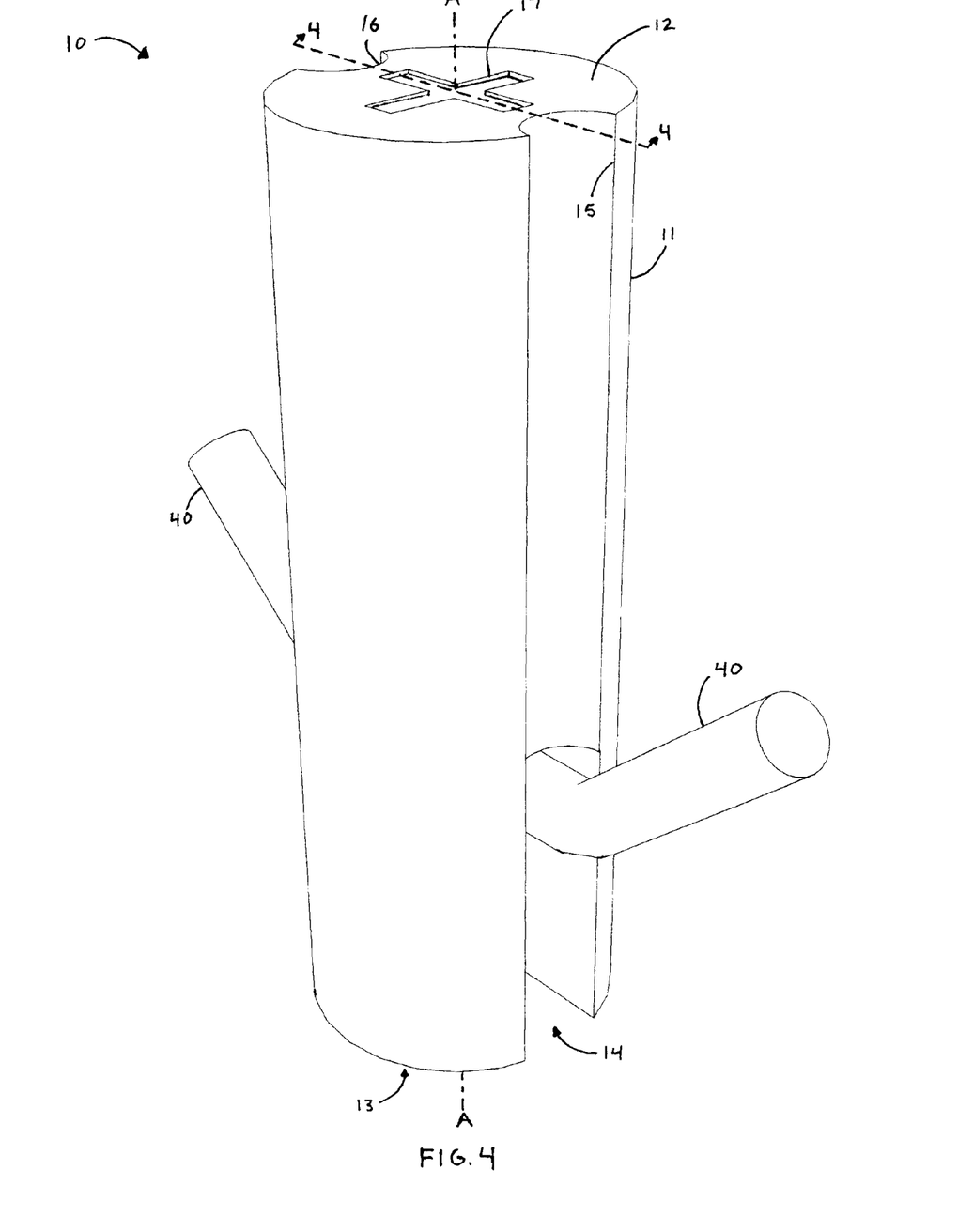
FIG. 4 is a side perspective view of the preferred embodiment of the suture anchor with a length of suture loaded in the anchor.
Figure 5:
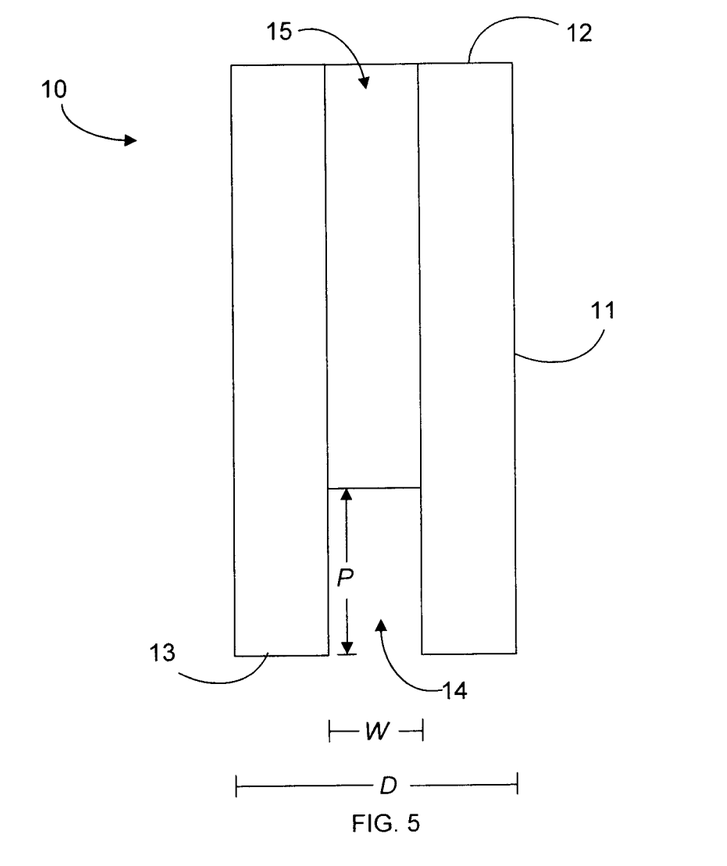
FIG. 5 is a right side view of the suture anchor of FIG. 4.
Figure 6:
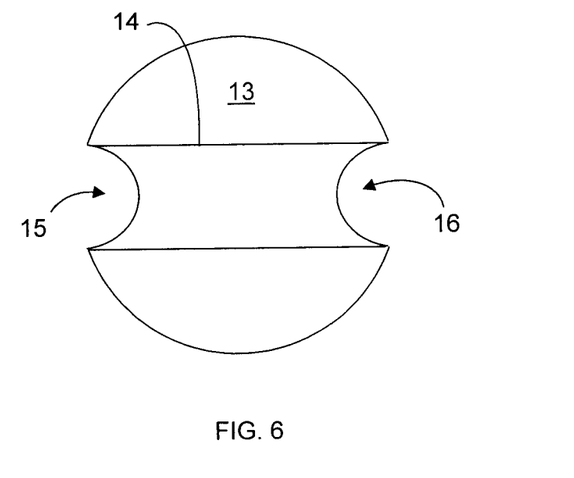
FIG. 6 is a bottom view of the suture anchor of FIG. 4.
Figure 7:
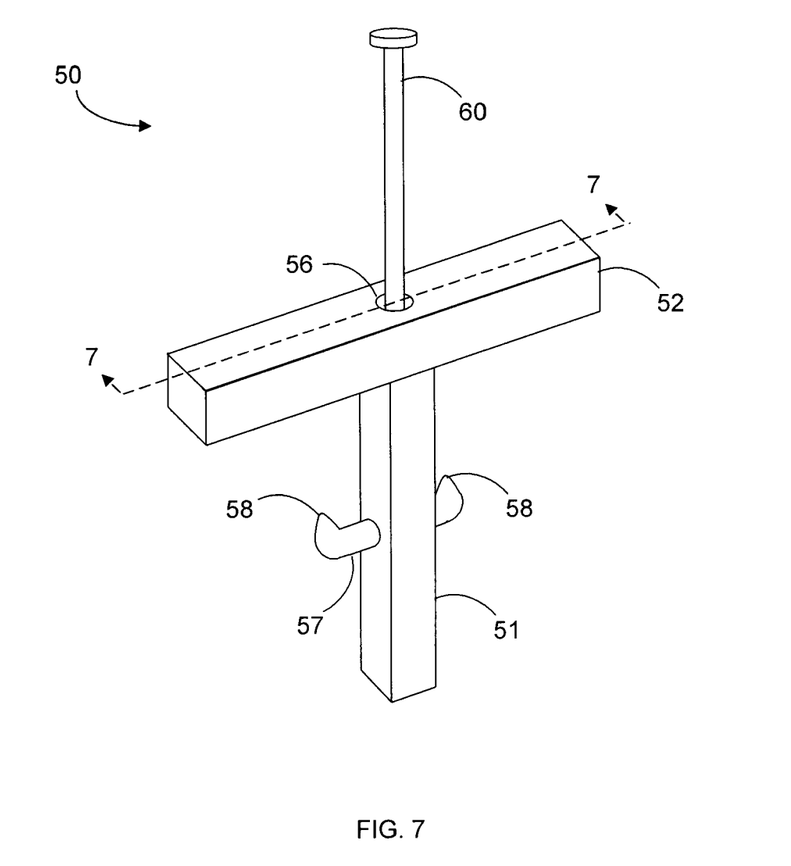
FIG. 7 a top perspective view of an insertion tool used in the surgical system.
Figure 8:
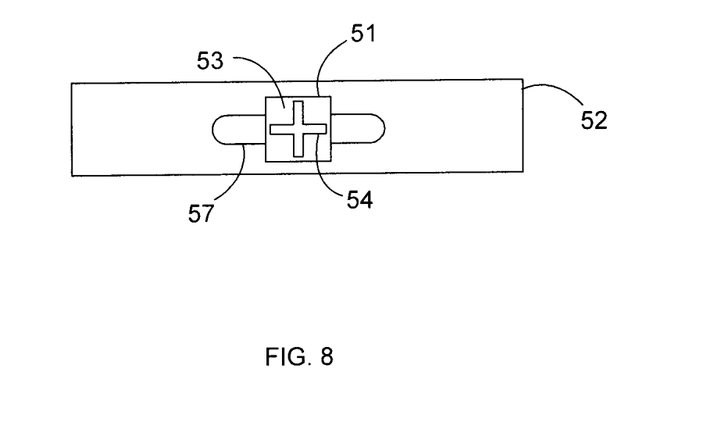
FIG. 8 is a bottom view of the insertion tool of FIG. 7

A retainer 14 is formed into the anchor body 11 and configured to retain one or more sutures 40 in place when the anchor 10 is implanted. The retainer 11 may be formed through the anchor body 11, or may be formed into the distal end 13 of the anchor body 11. Referring to FIGS. 1-3, a retainer 14 that passes through the anchor body 11 is loaded with suture 40 by threading a loose end of the suture 40 through the retainer 14 and pulling the end until the desired length of suture 40 is played out on either side of the anchor 10. Preferably, however, the retainer 14 is a suture slot formed into the distal end 13 and spanning the diameter of the anchor body 11. See FIGS. 4-6. This embodiment of the anchor 10 is easier to load because threading of the suture 40 through the retainer 14 is not necessary; rather, the suture 40 is inserted into the slot at the desired point along the length of the suture 40.

The size and shape of the retainer 14 and its location on the anchor body 11 may depend on the number, length, and type of sutures 40 used, and may further depend on certain properties of the anchor 10, including the anchor's 10 size, shape, and composition. A retainer 14 that passes through the anchor body 11, as in FIG. 1, may have a circular, ovular, triangular, square, or otherwise polygonal profile, and may be uniform or variable. Such a retainer 14 may be positioned between the proximal end 12 and the distal end 13, at a distance from the proximal end 12 that is favorable to the intended use of the anchor. Specifically, positioning the retainer 14 close to the proximal end 12 increases the ease of loading the anchor 12 with sutures 40 after implantation because a shorter length must be played out before the loose end of the suture 40 emerges from the opposite end of the retainer 14. On the other hand, positioning the retainer 14 further from the proximal end 12 increases the anchor's resistance to tensile forces and better protects against the suture tearing through the anchor 10 because there is more material between the suture 40 and the proximal end 12.

Referring again to FIGS. 4-6, a retainer 14 that is formed into the distal end 13 may have a concave, triangular, square, or rectangular profile, or another similar shape. Preferably, the retainer 14 has a rectangular profile and is wide enough to allow insertion of multiple sutures 40. Preferably, the width W of the retainer 14 is between 10% and 33% of the diameter D of the anchor 10, and is most preferably 33%. The preferred depth P may be referred to as a percentage of the length of the anchor body 11, and may be as long as 80% of the length of the anchor body 11. A deeper retainer 14 provides shorter channels 15, 16, and so less of the suture 40 contacts the anchor 10. However, the anchor's 10 resistance to pullout decreases as the proximity of the suture 40 to the proximal end 12 increases. The depth P is therefore preferably in the range of. 10% to 25% of the length of the anchor body 11, which is deep enough to retain sutures 40 while keeping a substantial portion of the anchor body 11 above the suture 40 to prevent pullout.

One or more channels 15, 16 may be formed into the exterior surface of the anchor body 11, the exterior surface being the surface that contacts the living bone on insertion. The channels 15, 16 provide access to the implant site to perform one or more functions as described below. The channels 15, 16 preferably connect the retainer 14 to the proximal end 12. In some embodiments, the channels 15, 16 may extend past the retainer 14, and may further extend to the distal end 13. Preferably, the channels 15, 16 are straight, and most preferably are formed substantially parallel to the axis A-A of the anchor body 11. Alternatively, one or more of the channels may be curved or zigzagged or otherwise askew.

The channels 15, 16 may have multiple functions. One function is to inject a compound, such as filler material or an adhesive, into any empty space behind the anchor 10 once the anchor 10 is implanted. For this function it is not necessary to have multiple channels 15; a single channel 15 that extends from the proximal end 12 to the distal end 13 is sufficient. Additionally, it is not necessary that the channel 15 connect to the retainer 14 if the sole purpose of the channel 15 is to inject a compound. For this function, the channel 15 is shaped to accommodate an injecting tool, such as a syringe. See FIGS. 8A-B and the description below.

Another function of the channels 15, 16 is to form, essentially, a passage from the proximal end 12 of the anchor body 11 down into the implant site, through the retainer 14, and back to the proximal end 12. See FIGS. 1-6, where the passage is formed by a first channel 15 connecting to one end of the retainer 14, and a second channel 16 connecting to the other end of the retainer 14, with both channels 15, 16 extending to the proximal end 12. The passage may be used to maintain the sutures 40 while the anchor 10 is implanted, without removing the anchor 10. Maintaining the sutures 40 may include removing a damaged or unwanted suture 40, and adjusting the position of a suture 40 in the retainer 14. The channels 15, 16 therefore have a width, and depth relative to the surface of the anchor body 11, that can accommodate the desired number and width of sutures 40. As illustrated, the channels 15, 16 are preferably concave. Alternatively, the channels 15, 16 may have a triangular, rectangular, or other polygonal profile. In the preferred embodiment, there are two channels 15, 16 positioned opposite, or 180 degrees from each other on the anchor body 11.

The anchor body 11 may be made of any material now known or later developed to be used for bone implants, including metal, polymers such as polylactic acid, bioabsorbable compounds, compounds comprising processed cortical bone, and machined cortical bone. Preferably, the anchor body 11 is machined from a single piece of cortical bone sourced from a human cadaver. Once implanted, it is expected that the preferred anchor 10 will expand by about 3% of its size, which is sufficient to secure the anchor 10 in place by interference fit. Additionally, new bone tissue from the living bone forms on the surface and into the porous structure of the anchor 10. It is further theorized that additional chemical bonds form between the living bone and the anchor 10 along the contacting surfaces, further holding the anchor 10 in place and absorbing the anchor 10.

It is contemplated in the present invention to provide the inventive channels and slot-shaped retainer 14 to existing and future-developed suture anchor designs. Because a suture anchor may be used at substantially any location in the body, the properties of the anchor 10, including the size, shape, and composition of the anchor body 11, retainer 14, and one or more channels 15, 16, may depend on the intended use of the anchor 10. The intended use may be defined by one or more of: the bone into which the anchor 10 will be implanted; the condition of the bone; the location, entry angle, width, and depth of the hole into which the anchor 10 will be inserted; whether the anchor 10 is replacing a failed implant; the tissue to which the suture 40 is to be attached, and the properties and condition of that tissue; the number, width, and composition of the sutures 40, and the desired performance characteristics of the anchor 10. The present inventive anchor 10 may be implanted into any bone and used to reattach any tissue.

Preferably, the anchor 10 is loaded with suture 40 and installed into the implantation site using an insertion tool 50. Referring to FIGS. 7, 8, and 9A-B, the insertion tool 50 has a shaft 51 with a handle 52 attached to its proximal end. The face 53 of the distal end of the shaft 51 contacts the proximal end 12 of the anchor 10. Preferably, the face 53 comprises a protruding alignment guide 54 that cooperates with the insertion guide 17 on the anchor 10. A reel duct 55 passes through the shaft 51 substantially orthogonally to the axis of the shaft 51, and a pin duct 56 is positioned substantially coaxially with the shaft 51, passing through the handle 52 and extending into the shaft 51, intersecting the reel duct 55 and terminating at a point that is distal of the reel duct 55. The reel duct 55 receives a reel 57 that is slightly smaller than the diameter of the reel duct 55 so it may rotate freely in the reel duct 55. The reel 57 has a plurality of locking holes 59 passing through the reel 57 and aligned with the pin duct 56. Preferably, the locking holes 59 are spaced uniformly around the reel 57 so that each locking hole 59 has a diametrically opposed locking hole 59. A pin 60 having a pin shaft 61 and a pin head 62 fits into the pin duct 56 such that the head 62 contacts the top of the handle 52 when the pin 60 is fully inserted. The pin 60 passes through diametrically opposed locking holes 59 to prevent the reel 57 from rotating.

Figure 9A:
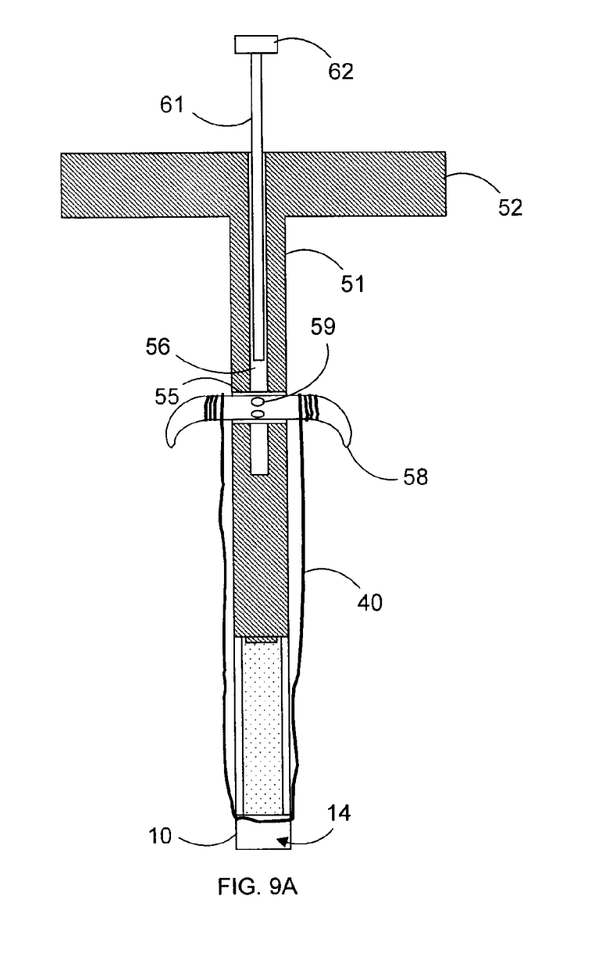
FIGS. 9A-9B illustrate a front view of using the insertion tool of FIG. 7 to load a suture into the preferred anchor, with the anchor shown in cross-section taken along line 4-4 of FIG. 4, and the shaft and handle of the insertion tool shown in cross-section taken along line 7-7 of FIG. 7.
Figure 9B:
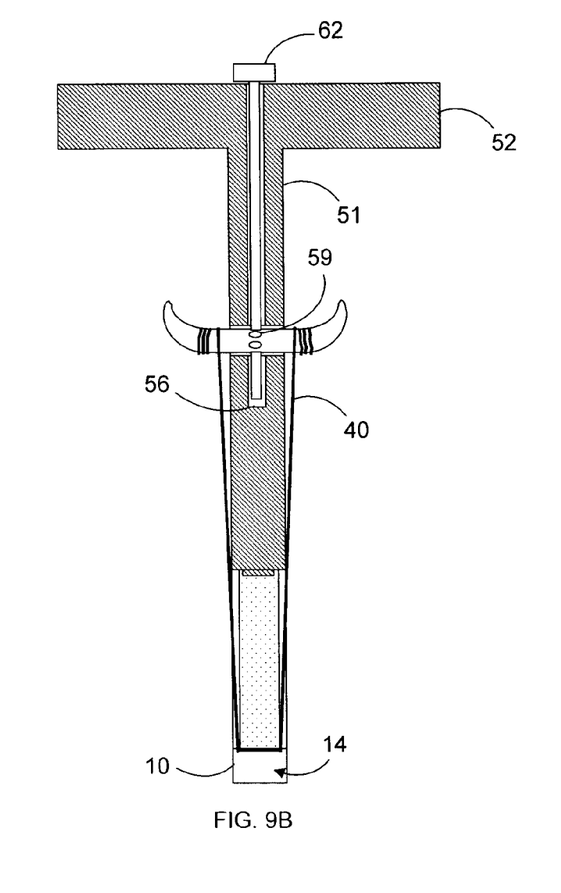

Referring to FIGS. 9A and 9B, the insertion tool 50 is configured to retain the anchor 10 in a desired alignment and hold the suture 40 under slight tension in the retainer 14 and along the channels 15, 16 for installation. The alignment guide 54 cooperates with the insertion guide 17 to align the channels 15, 16 with the reel 57. The suture 40 is loaded by inserting it into the retainer 14 at the desired point along the length of the suture, typically the midpoint. The loose ends, which may be attached to suture needles as is known in the art, are then wrapped at least once around the reel 57. The ends may be wrapped by hand, but preferably the ends are wrapped around the reel ends 58 and the reel 57 is rotated to take up the slack in the suture 40. The suture 40 is wrapped until slight tension retains the suture 40 in the retainer 14 and at least partially within the channels 15, 16. Then, the pin 60 is inserted into the pin duct 56, passing through a pair of diametrically opposed locking holes 59 to lock the reel 57 in place. Once the anchor 10 is installed in the implantation site, the pin 60 is pulled out, unlocking the reel 57. The insertion tool 50 is then withdrawn, and as it is withdrawn the suture 40 unspools from the reel 57, leaving the loose ends available for tying to the tissue.

Figure 10A:
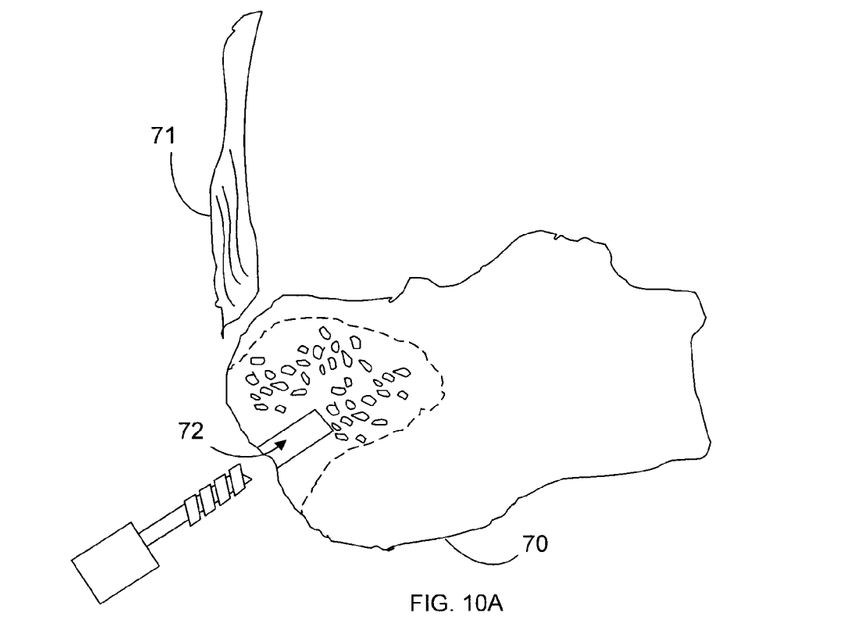
FIGS. 10A-10C are partial cross-sectional side views of a method of implanting the preferred suture anchor in a human calcaneus.
Figure 10B:
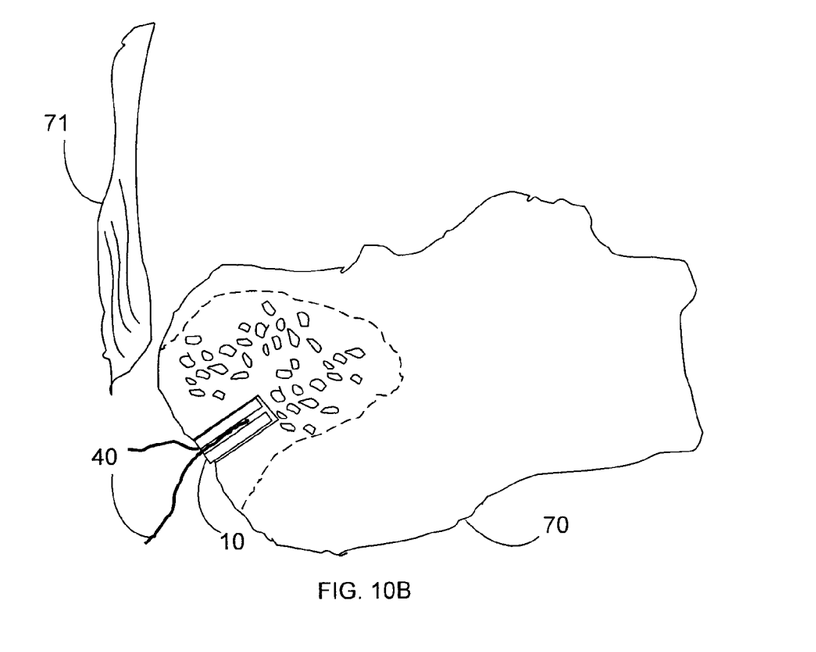
Figure 10C:
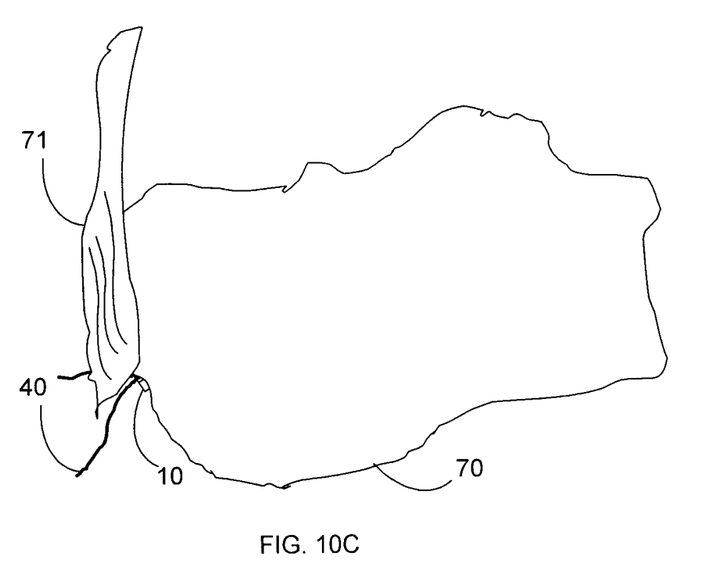

By example, there is illustrated in FIGS. 10A-C a method of using the preferred anchor 10 in a human ankle reconstructive surgery. FIG. 10A illustrates the calcaneal tendon 71 having been severed from its attachment point to the calcaneus 70, which is illustrated in partial cross-section. The preferred anchor 10 is used to reattach the tendon. In this example, the preferred anchor 10 has a diameter of 6 mm and a length of 12 mm. First, as shown in FIG. 10A, a hole 72 is drilled into the calcaneus 70 so that the axis of the hole 72 is at an angle of between 90 and 135 degrees from the suture 40 when it is tied in place. This angle is in accordance with the "deadman" theory developed by Burkhart. Parisien 8:76 (Third Edition). The hole 72 is substantially the same diameter and length as the anchor 10.

Then, the anchor 10 is loaded with a size 2-0 suture 40, which has a diameter of 0.3 mm, using the insertion tool 50 as shown in FIGS. 9A-B and described above. Once the anchor 10 is loaded and positioned on the insertion tool 50, the distal end 13 is placed at the mouth of the hole 72. The physician applies pressure to the handle 52, pushing the anchor 10 into the hole 72. Referring again to FIG. 10B, when the proximal end 12 of the anchor 10 is substantially flush with the surface of the calcaneus 70, the pin 60 is pulled from the locked position and the insertion tool 50 is withdrawn, spooling the suture off of the reel 57. The suture 40 passes out of the channels 15, 16, leaving the loose ends to be attached to the tendon 71 as is known in the art. The anchor 10 expands, securing itself in the hole 72. Then, as shown in FIG. 10C, the tendon 71 is positioned so it may be sewn into place with the suture 40.

Figure 11A:
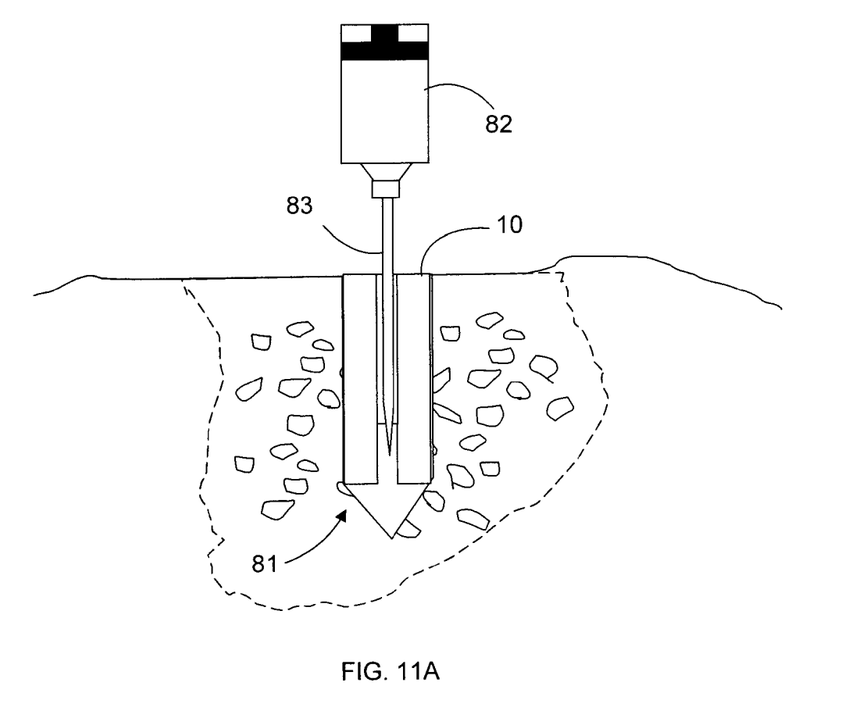
FIGS. 11A-11B are cross-section side views of a method of filling a bone void behind the preferred suture anchor.
Figure 11B:
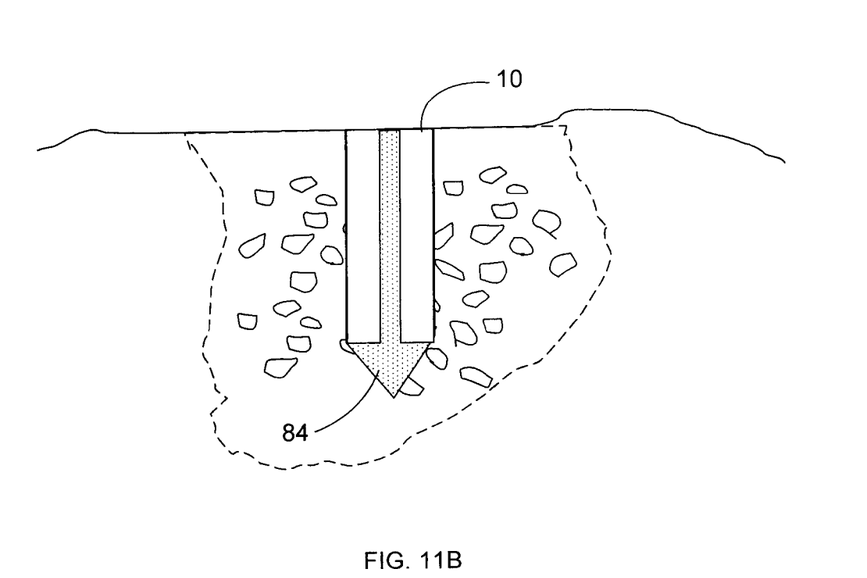

If the suture 40 must be removed due to breakage, damage, or poor placement of the anchor 10, the physician can detach the suture 40 from one or both suture needles and pull the suture 40 out of the tendon 71 and out of the anchor 10 through the channels 15, 16. Referring to FIGS. 11A-B, the physician may then fill in any bone voids in the implantation site, such as a drill tip void 81 left from drilling the hole 72. The channels 15, 16 themselves may also be filled. In FIG. 11A, a needle 83 of a syringe 82 filled with bone cement 84 is inserted into the channel 15. Depressing the plunger fills the drill tip void 81 with bone cement 84, and the bone cement 84 also fills the second channel (not shown) and, finally, the first channel 15 as the needle 83 is withdrawn. This completely fills the implantation site. See FIG. 11B. Once the bone cement 84 has set, the implantation site may be redrilled for a new anchor 10 if desired.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

I claim:

1. A method of attaching tissue to a bone, the method comprising:
   retaining a suture in a suture anchor comprising:
   a) a body having a distal end and a proximal end;
   b) a retainer configured to retain a suture within the suture anchor;
   c) a first channel formed into an exterior surface of the body and extending from the proximal end of the body to the retainer; and
   d) a second channel formed into the exterior surface of the body and extending from the proximal end of the body to the retainer;
   the retaining comprising:
   a) inserting the suture into the retainer;
   b) aligning the suture anchor with an insertion device, the insertion device comprising:
      i. a shaft having a proximal end and a distal end;
      ii. a handle attached to the shaft at the proximal end;
      iii. a cylindrical reel passing through the shaft and having an axis around which the reel rotates; and
      iv. a locking pin extending into the shaft coaxially with the shaft, and configured to be inserted into the reel to prevent the reel from rotating;
   c) attaching the suture to the reel;
   d) winding excess length of suture around the reel until the suture is under slight tension; and
   e) inserting the locking pin into the reel;
   installing the suture anchor into an implant site in the bone;
   using the first channel to access the implant site; and
   securing the tissue to the suture.

2. The method of claim 1 wherein installing the suture anchor into an implant site in the bone comprises:
   a) using the insertion device to align the suture anchor with the implant site;
   b) applying force to the handle to insert the suture anchor into the implant site;
   c) removing the locking pin from the reel; and
   d) withdrawing the insertion device to unwind the excess length of suture.

3. The method of claim 2 wherein the retainer is a slot formed into the distal end of the body.

* * * * *